(12) United States Patent
Hignight et al.

(10) Patent No.: US 7,368,639 B2
(45) Date of Patent: May 6, 2008

(54) MEADOW FESCUE VARIETY AMF107

(76) Inventors: Kenneth Hignight, 613 S. 3rd, Jefferson, OR (US) 97352; Debra Rush, 3483 Madison, Albany, OR (US) 97322

( * ) Notice: Subject to any disclaimer, the term of this patent is extended or adjusted under 35 U.S.C. 154(b) by 0 days.

(21) Appl. No.: 11/281,288

(22) Filed: Nov. 17, 2005

(65) Prior Publication Data

US 2006/0143742 A1  Jun. 29, 2006

Related U.S. Application Data

(60) Provisional application No. 60/638,895, filed on Dec. 23, 2004.

(51) Int. Cl.
*A01H 5/00* (2006.01)
*A01H 5/10* (2006.01)
*A01H 1/00* (2006.01)

(52) U.S. Cl. .................. 800/320; 800/260; 800/298

(58) Field of Classification Search ................ 800/260, 800/298, 320, 323
See application file for complete search history.

(56) References Cited

OTHER PUBLICATIONS

Fehr. 1987. Principles of cultivar development, vol. 1, Theory and Technique, p. 519.*
Harivandi. 1986. California Turfgrass Culture, vol. 36, No. 1-4, pp. 1-4.*
Casler et al. 2000. Crop Sci. 40: 248-255.*
Haugland, E., Tawfiq, M., Root and Shoot competition between established grass species and newly sown seedlings during spring growth, Blackwell Science Ltd., 2001, 193-199, 56.
Berg, T., Studies on Hybrids between perennial ryegrass (Lolium Perenne L.) and meadow fescue (Fesluca Pratenisis Huds.), Agricultural University of Norway, 1978, vol. 58.
Kopecky, D., Lukaszewski, A.J., Gibeault, V., Reduction of Ploidy Level by Androgenesis in Intergeneric Lolium-Festuca Hybrids for turf grass breeding, Crop Science, 2005, 274-281, 45, Crop Science Society of America, Wisconsin.
Fang, C., Aamlid, T.S., Jorgensen, O., Rognli, O.A., Phenotypic and genotypic variation in seed production traits within a full-sib family of meadow fescue, Plant Breeding, 2004, 241-246, 123, Blackwell Verilag, Berlin.
Buckner, R.C., Powell, J.B., Frakes, R.V., Tall Fescue, Crop Science, 1979, Soil Science Society of America, Inc., Wisconsin.
Casler, M.D., Van Santen, E., Performance of Meadow Fescue Accession under Management-Intensive Grazing, Crop Science, 2001, 1946-1953, 41.
Fisher, G.G., Aberystwyth "S" strains of grasses, The Journal of the Sports Turf Research Institute, 1951, 50-55, 27, The Sports Turf Research Institute, Bingley, England.
Handoll, C., Grass variety trials, The Journal of the Sports Turf Research Institute, 1966, 49-53, 42, The Sports Turf Research Institute, Bingley, England.
Arakeri, H.R., Schmid, A.R., Cold Resistance of Various Legumes and Grasses in Early Stages of Growth, 1949.

* cited by examiner

*Primary Examiner*—David H. Kruse
*Assistant Examiner*—Keith O. Robinson

(57) ABSTRACT

A meadow fescue variety known as breeder's code AM 107 and seed used to produce the grass are provided. Methods of using the grass plant and the seed are also provided. This grass is suitable for use in turf (lawns, golf courses, sod, and other areas where excellent turf quality is desired) and for overseeing Bermudagrass. This grass has superior cold tolerance and has a rapid transition.

9 Claims, No Drawings

MEADOW FESCUE VARIETY AMF107

This application claims priority to U.S. patent application Ser. No. 60/638,895, filed Dec. 23, 2004.

BACKGROUND OF THE INVENTION

1. Field of the Invention

This invention relates to cultivated varieties of true breeding, stable, meadow fescue, for use as a short lived, improved turfgrass on golf courses, athletic fields and other areas using seeded turfgrasses.

2. Background of the Art

Meadow fescue is not widely used as a turfgrass. It has been used in limited amounts in colder regions since it has good cold tolerance. It has been used mostly as a forage grass but has not been considered a desirable turfgrass. A few turfgrass species have been developed for permanent turf use but no cultivators have been developed for overseeing of dormant warm-season grasses.

A stable turfgrass variety of meadow fescue would be desirable for several applications. It would provide a permanent turf in areas where tall fescue and perennial rye grass lack the cold tolerance to persist. It would also be a desirable grass for use in overseeing of dormant warm season grasses since its lack of heat tolerance allows for a smooth transition for the warm-season grass. The meadow fescue will provide a green cover during the winter months but will die out when the temperatures increase which allow the warm-season grass to grow.

For many southern golf courses planted with Bermuda grass, a standard practice is to oversexed every fall with perennial rye grass. Perennial rye grass provides an outstanding turf cover during the cool winter months. However, perennial rye grass is very persistent and does not easily die out and give way for the re-emerging Bermuda grass in the spring when warm weather returns.

What turf managers could utilize is a cultivator that establishes quickly, has an attractive color which blends well with Bermuda grass, has superior cold tolerance over perennial rye grass and has a rapid transition. Currently there are two major grasses used in overseeing, annual and perennial rye grass. These species lack sufficient cold tolerance and often suffer winter injury.

SUMMARY OF THE INVENTION

The invention consists of a new variety of meadow fescue identified under the breeder's code AM107. AM107 is a true breeding, stable meadow fescue with high cold tolerance. It is a desirable grass for use in overseeing of dormant warm season grasses, providing a green cover during winter months, but dying out when the temperature increases thereby allowing the warm season grasses to grow. The meadow fescue is different from all known species of meadow fescue in that it has a leaf blade width of less than 8 mm, a mature plant height of less than 125 cm, a panics length of less than 69 cm, a lemma length of less than 6.25 mm, a glumae length of less than 4.5 mm, and a panics length (whorl to apex) of less than 228 mm. The meadow fescue of the present invention is different from all known species of meadow fescue in that it has a seed weight of less than 2400 grams per 1000 seeds, less than 7.5 florets per spike let, and less than 51 spike lets per panics.

DETAILED DESCRIPTION OF A PREFERRED EMBODIMENT

As used in the broad context in grasses, the term "overseeing" relates to the process of placing grass seed over an existing stand of turfgrass. As used in the context of this document, the term "overseeing" relates only to the use of cool-season grasses sown into an existing warm season grass turf, for the purpose of having a green cover during the winter months when the warm-season grass is dormant.

| Species Used | Establishment | Color | Transition |
|---|---|---|---|
| Annual ryegrass | E | P | E |
| Fine fescue | P | F | G |
| Perennial ryegrass | VG | E | P-F |
| Poa trivialis | F | G | G |
| Intermediate ryegrass | VG | F-G | G |
| Meadow fescue | VG | G | E |

E = excellent
VG = very good
G = good
F = fair
P = poor

Key Elements in Overseeing Turf grass.

Establishment—It is important in an overseeing grass to have rapid establishment. This includes a quick germination of the seed and the ability to tiller into areas adjacent to the next seedling.

Color—Many users of overseeing grasses prefer a dark green color. A light color grass can be made darker by applying iron. However, the user generally prefers to not do this unless the grass is too light in color.

Transition—A desirable transition grass is one that will die completely when the warm season grass is starting to reach its peak performance. The overseeing grass cannot die too quickly in the spring before the warm-season grass has an opportunity to grow.

Discussion of Current Species Used.

Annual rye grass—Annual rye grass was used extensively for overseeing prior to 1970. With breeding improvements of perennial rye grass the use of annual rye grass has declined. Annual rye grass has an excellent germination rate but lacks tilling ability. Annual rye grass is light in color and usually transitions too abruptly. The course leaf texture and very fast growth rate are undesirable.

Perennial rye grass—Perennial rye grass has a quick germination. It germinates slower than annual rye grass but still within an acceptable range for the user. It has a very good tilling ability but in some cases it is too aggressive resulting in damage to the warm season grass. Newer cultivators of perennial rye grass have excellent, dark green, color. The newer varieties of perennial rye grass which are being sold as overseeing grasses were developed for permanent turf use. The result is a poor transitions ability. This has resulted in the use of chemical applications to remove the perennial rye grass. When this is necessary the turf has damage for several weeks, until the warm-season grass can recover.

Intermediate rye grass—Intermediate rye grass performance is more difficult to predict. It is a cross between annual and perennial rye grass. If only one cross is made the performance is most similar to annual rye grass. Each successive back cross to perennial rye grass results in performance similar to perennial rye grass. A problem with current intermediate rye grass is that it often transitions too rapidly, before the warm-season grass has a desirable level of performance.

*Poi trivializes* and Fine fescues—Both of these have slow germination and establishment. Because of this they are commonly used in mixtures with other grasses. The cost of producing these grasses is higher and as a result they are not usually used alone. They both have good transitions ability.

Meadow fescue—Meadow fescues have several attributes that are appealing for overseeing. It has rapid establishment and smooth transition. The establishment is similar to perennial rye grass. The transition is slower than annual rye grass but much quicker than perennial. It has an ability to form a dense turf. The color is similar to Bermuda grass (warm-season) so that the spring transition is not noticeable.

Morphological Descriptors for Meadow Fence

Heading Date—measured when 3 inflorescences emerge 1 inch from the sheath. Recorded as number of days after April 1.

Genetic Color—the measure of the amount of lightness or darkness of green color. Recorded as a 1-9 subjective rating where 9=dark.

Inflorescence—the flowering portion of a grass plant.

Panics—the type of inflorescence found in meadow and tall fescue.

Panics Length—the length of a panics. Measured from the first node subtending the flag leaf to the apex of the inflorescence in cm.

Leaf Blade—the flattened portion of a grass leaf located above the leaf sheath.

Leaf Blade Anthocyonin—the degree of red pigmentation found in the leaf blade. Measured on the first leaf blade subtending the flag leaf. 1=absent, 9=present Leaf Blade Margin Roughness—the degree of roughness on the edge of a leaf blade. Measured on the first leaf subtending the flag leaf. 1=smooth, 5=semi-rough, 9 =rough Leaf Blade Length—the length of the leaf blade. Measured on the first leaf subtending the flag leaf in cm.

Leaf Blade Width—measure of the width of the first blade subtending the flag leaf in mm taken 1 cm from the collar.

Leaf Blade Height—the height of the leaf blade from the ground to the collar in cm.

Leaf Sheath Length—the length of the leaf sheath. Measured on the first leaf subtending the flag leaf in cm.

Flag Leaf—the first leaf blade subtending the inflorescence.

Flag Leaf Length—the total length of a flag leaf which includes the sheath and blade. Measured from the uppermost node to the end of the upper-most blade in cm.

Flag Leaf Width—the measure of the width of the flag leaf blade taken 1 cm from the collar of the flag leaf in mm.

Flag Leaf Height—the height of the flag leaf. Measured from the ground to the collar of the flag leaf in cm.

Flag Leaf Sheath Length—the sheath length of the flag leaf. Measured from the node to the collar in cm.

Mature Plant Height—the height in cm of a mature plant from the ground to the apex of the inflorescence. Measured after anthesis.

Internode—the distance between two nodes.

Glumae—the first pair of bracts at the base of a spike let.

Spike let—the basic unit of a grass inflorescence, includes glumes, lemmas, paleas and reproductive organs.

Floret—the portion of the spike let which may include lemma, palea and reproductive organs.

Lemma—an odd nerved bract above the glumes.

Seed Size—the relative size of seeds usually measured by determining the number of seeds per pound.

1000-seed weight—the weight of 1,000 whole seeds.

Turf grass Density—the number of tillers per unit area of a turfgrass sward.

Turf—a covering of mowed vegetation usually a grass.

Turf grass—a species or cultivator of grass which is a mowed turf.

Turf Color—a visual or digital analysis score of the turfgrass community. When visual the color is measured on a scale of 1-9 with 9 being dark.

Turf Quality—the degree to which a turf conforms to a standard of uniformity, density, texture, growth habit, color and is generally taken as subjective data on a 1-9 scale with 9 being the best quality.

EXAMPLES

The following examples are furnished to further illustrate the present invention and are not intended to limit the invention beyond the examples set forth in the appended claim.

Example 1

Development of AM107

In 1994, the breeding research program that resulted in the meadow fescue variety, AM107 was initiated. The following breeding history describes the procedures used (see Table 1):

In September, 1994 a single spaced plant nursery was established. This nursery contained 200 plants each of Belimo, Bundy, Predix, Bartran, and ecotypes collected from seven European countries. At the same time 14 different ecotypes from Europe were established in a turf trial, located near Salem, N.J.

In May, 1995 the single spaced plant nursery was evaluated for; heading date, freedom from disease (*Puccinia graminis*), genetic color, crown density, and leaf texture.

In late August, thirty-two new crossing populations were formed. These new populations were grouped based on pedigree, heading date, freedom from disease (*Puccinia graminis*), genetic color, crown density, and leaf texture. These new populations were moved together to isolated crossing blocks. In July the 32 populations were harvested.

In September a new single spaced plant nursery was established of the 32 populations, with 300 plants per population. Five forage cultivators from Europe were also added to this nursery, with 300 plants of each cultivator. The five forage cultivators were Roznovska, Swift, Barmondo, Stella, and Cosmos.

In September, 1996 twenty survivors were removed from each entry of the 1994 turf trial, near Salem, N.J. The plants were shipped back to Albany, Oreg., for increase. Each of the 14 lines was increased in isolation. In July, 1997 the 14 lines were harvested.

In May, 1997 the single spaced plant nursery was evaluated for; heading date, freedom from disease (*Puccinia graminis*), genetic color, crown density, and leaf texture. In late August, twenty two new crossing populations were formed. These new populations were grouped based on pedigree, heading date, freedom from disease (*Puccinia graminis*), genetic color, crown density, and leaf texture. These new populations were moved together in late September to isolated crossing blocks.

In July, 1998 the crossing groups were harvested. In September a new single spaced plant nursery was established. This nursery included all the entries from the turf trial (14 entries) and the material cycled through the single spaced plant nurseries (22 entries).

In May, 1999 the single spaced plant nursery was evaluated for; heading date, freedom from disease (*Puccinia graminis*), genetic color, crown density, and leaf texture. In late August, eighteen new crossing populations were formed. These new populations were grouped based on pedigree, heading date, freedom from disease (*Puccinia graminis*), genetic color, crown density, and leaf texture. These new populations were moved together in late September to isolated crossing blocks.

In July, 2000 the crossing groups were harvested. In September a turf trial was established near Salem, N.J.

In September, 2001 twenty survivors were removed from 9 entries of the 2000 turf trial, near Salem, N.J. These nine entries exhibited the best turf characteristics; color, density, and leaf texture. The plants were shipped back to Albany, Oreg. for increase. Each line was increased in isolation.

In late July, 2002 the isolated blocks were harvested. In September a new single spaced plant nursery was established.

In May, 2003 the single spaced plant nursery was evaluated for; heading date, freedom from disease (*Puccinia graminis*), genetic color, crown density, and leaf texture. The new population was grouped based on heading date, freedom from disease (*Puccinia graminis*), genetic color, crown density, and leaf texture. The new population was moved together in June to an isolated crossing block. In July, 2003 the crossing group was harvested.

In late September, 2003 a bulk population of the pre-breeder seed was established in isolation. A morphological nursery was also established. This nursery contained five entries, twenty plants per replication, three replications; for a total of 60 plants per entry. The morphological nursery was established to aid in the description and distinctness of AM107.

In May, 2004 the pre-breeder seed block was evaluated for off-type or variant plants. Eight percent of the plants were removed based on presence of disease (*Puccinia graminis*), light genetic color, and course leaf texture. In mid-July the block was harvest and designated AM107, breeder seed.

After breeder seed was harvested, over-seeding turf trials were planted in Arkansas, Arizona, and Alabama.

TABLE 1

| | Breeding Scheme | |
|---|---|---|
| 1994 | Establish single spaced plant nursery | Establish turf trial near Salem, NJ |
| 1995 | New crossing populations formed | Turf trial evaluated |
| 1996 | New populations harvested and new single spaced plant nursery established | Survivors removed from turf trial. |
| 1997 | New crossing populations formed. | Survivors harvested. |
| 1998 | New populations harvested and new single spaced plant nursery established | Survivors added to single spaced plant nursery. |
| 1999 | New crossing populations formed | ← |
| 2000 | New populations harvested and new turf trial established near Salem, NJ | ← |
| 2001 | Survivors removed from turf trial. | ← |
| 2002 | Survivors harvested and new single spaced plant nursery established. | ← |
| 2003 | New populations formed in the spring and harvest in the summer. A pre-breeder seed block established. | ← |
| 2004 | Pre-breeder seed block harvested = AMF107 | ← |

Example 2

AM107 is the first meadow fescue used for turf overseeing applications. AM107 is also the first meadow fescue which exhibits a fine leaf texture and dark leaf color, which is more similar to current cool season turf (i.e. perennial rye grass and tall fescue). Leaf color is the degree of lightness or darkness of green of the leaf blades of single plants and in turf. A dark green color is preferred over lighter shades because it gives an impression of a more healthy and robust turf.

Turf color can be evaluated in different ways. a) the relative color of the different cultivators was scored using a 1-9 visual scale, 9 being the darkest green. Table 2 shows the comparisons between the meadow fescue, perennial rye grass, and tall fescue. b) Digital analysis can also be used to determine color. A digital picture is taken of the turf. The software program Sigma Scan is used to convert the pixel image to a standard color wheel (hue, saturation, and brightness). It then generates a number on a 1-9 scale, with 9 being the darkest green.

Both visual and digital comparisons (Tables 2 and 3) show that AM107 is equal to current tall fescue and perennial rye grass cultivators available on the market. The turf color of AM107 is most similar to Applaud perennial rye grass.

Table 2 shown below, the visual comparisons are given for several cultivators taken in Albany, Oreg. during 2004/2005. The ratings are based on the following: 1=light green; 3=medium-light green; 5=medium green; 7=medium-dark green; 9=dark green.

TABLE 2

Visual Color Comparisons
(Albany, Oregon - 2004/2005)

| Species | Variety | Rating |
| --- | --- | --- |
| Meadow Fescue (turf) | AMF107 | 7.17 |
| Meadow Fescue (forage) | Ricardo | 2.03 |
| Tall Fescue (turf) | Rebel Exeda | 6.33 |
| Perennial Ryegrass (turf) | Applaud | 6.76 |
| Perennial Ryegrass (turf) | Yorktown III | 4.59 |
| Perennial Ryegrass (forage) | Bastion | 4.92 |
| | LSD (0.05) | 0.57 |

In table 3 shown below, the digital ratings are given for several cultivators taken in Albany, Oreg. during 2004/2005.

TABLE 3

Digital Color Comparisons
(Albany, Oregon - 2004/2005)

| Species | Variety | Rating |
| --- | --- | --- |
| Meadow Fescue (turf) | AMF107 | 6.33 |
| Meadow Fescue (forage) | Ricardo | 3.06 |
| Tall Fescue (turf) | Rebel Exeda | 7.33 |
| Perennial Ryegrass (turf) | Applaud | 7.20 |
| Perennial Ryegrass (turf) | Yorktown III | 4.86 |
| Perennial Ryegrass (forage) | Bastion | 3.52 |
| | LSD (0.05) | 0.88 |

Example 3

AM107 is the first cultivator of meadow fescue with finer leaf blade characteristics comparable to turf type tall fescue. One of the desirable qualities of a cool season turf is the relative fineness of the leaf texture.

Table 4 gives the leaf blade width of AM107 in comparison to other cool season grasses. A wider leaf blade results in a more course appearance, which is undesirable. AM107 has a leaf blade width comparable to Forte', but is significantly different than the forage KY-31.

TABLE 4

Leaf Blade Width
(Albany, Oregon - 2004/2005)

| Species | Variety | Leaf Blade Width (mm) |
| --- | --- | --- |
| Meadow Fescue (turf) | AMF107 | 7.47 |
| Tall Fescue (turf) | Forte' | 6.57 |
| Tall Fescue (turf) | Rebel II | 8.07 |
| Tall Fescue (forage) | KY-31 | 9.83 |
| Perennial Ryegrass (turf) | Brightstar | 3.70 |
| Perennial Ryegrass (turf) | Amazing | 3.83 |
| | LSD (0.05) | 0.39 |

Table 5 shows the leaf blade length, height, and sheath length of AM107 compared to other cool season grasses.

TABLE 5

Leaf Blade Measurements
(Albany, Oregon - 2004/2005)

| Species | Variety | Length (cm) | Height (cm) | Sheath (cm) |
| --- | --- | --- | --- | --- |
| Meadow Fescue (turf) | AMF107 | 37.43 | 31.93 | 16.23 |
| Tall Fescue (turf) | Forte' | 35.63 | 23.27 | 14.47 |
| Tall Fescue (turf) | Rebel II | 45.80 | 31.00 | 18.33 |
| Tall Fescue (forage/turf) | KY-31 | 54.37 | 41.07 | 22.53 |
| Perennial Ryegrass (turf) | Brightstar | 20.30 | 17.43 | 6.97 |
| Perennial Ryegrass (turf) | Amazing | 20.00 | 19.40 | 6.87 |
| | LSD (0.05) | 1.48 | 1.88 | 0.50 |

Example 4

AM107 is the first meadow fescue with a reduced plant height that is more similar to turf type tall fescue. Forage grasses have more significant mature plant heights compared to grasses used for turf. In turf, a lower growth habit is more desirable because: a) faster vertical growth rate results in increased mowing, and b) more biomass is produced. For turf applications a faster growth rate and increased biomass are not favorable.

Table 6 shows AM107 is the first meadow fescue that has a reduced plant height which is significantly less than turf type tall fescue Rebel II and forage type KY-31

TABLE 6

Mature Plant Height
(Albany, Oregon - 2004/2005)

| Species | Variety | Mature Plant Height (cm) |
| --- | --- | --- |
| Meadow Fescue (turf) | AMF107 | 109.10 |
| Tall Fescue (turf) | Forte' | 107.30 |
| Tall Fescue (turf) | Rebel II | 128.17 |
| Tall Fescue (forage) | KY-31 | 147.37 |
| Perennial Ryegrass (turf) | Brightstar | 56.90 |
| Perennial Ryegrass (turf) | Amazing | 57.83 |
| | LSD (0.05) | 5.12 |

Example 5

AM107 is the first meadow fescue that the flag leaf characteristics are reduced. Forage grasses have been selected for increased plant size. Turf grasses have be selected for decreased plant size. The flag leaf characteristics: a) length; b) width; c) height; d) sheath length are an indicator of overall plant size.

Table 7 gives the flag leaf measurements compared to other cool season grasses and shows that the flag leaf characteristics; length, width, height, and sheath length of AM107 are shorter than forage grasses, but similar to turf type tall fescue.

TABLE 7

Flag Leaf Measurements
(Albany, Oregon - 2004/2005)

| Species | Flag Leaf Length (cm) | Flag Leaf Width (mm) | Flag Leaf Height (cm) | Flag Leaf Sheath Length (cm) |
|---|---|---|---|---|
| Meadow Fescue (turf) AMF107 | 41.13 | 6.87 | 65.20 | 23.73 |
| Tall Fescue (turf) Forte' | 39.07 | 5.33 | 54.80 | 24.93 |
| Tall Fescue (turf) Rebel II | 50.83 | 6.27 | 71.53 | 32.03 |
| Tall Fescue (forage/turf) KY-31 | 57.37 | 7.00 | 84.03 | 37.80 |
| Perennial Ryegrass (turf) Brightstar | 21.23 | 3.33 | 30.60 | 10.67 |
| Perennial Ryegrass (turf) Amazing | 21.83 | 3.43 | 33.10 | 10.43 |
| LSD 0.05 | 1.56 | 0.49 | 2.24 | 1.37 |

AM107 is the first meadow fescue that has a shorter panics length, similar to turf type tall fescue. Table 8 shows AM107 to have a shorter panics length similar to turf type tall fescue.

TABLE 8

Panicle Length
(Albany, Oregon - 2004/2005)

| Species | Variety | Panicle Length (cm) |
|---|---|---|
| Meadow Fescue (turf) | AMF107 | 67.33 |
| Tall Fescue (turf) | Forte' | 77.93 |
| Tall Fescue (turf) | Rebel II | 88.53 |
| Tall Fescue (forage) | KY-31 | 97.73 |
| Perennial Ryegrass (turf) | Brightstar | 35.77 |
| Perennial Ryegrass (turf) | Amazing | 34.90 |
| | LSD (0.05) | 3.44 |

Example 6

AM107 is the first meadow fescue with a seed size more similar to turf type tall fescue. Seed size is an important trait in the turfgrass industry for two reasons: a) a seed of smaller size allows for ease of distribution over the seed bed; b) a smaller seed relates to more seeds per pound. This results in more seeds being disbursed over the seeding area. This allows more seeds to germinate and establish in a given area. Seed size can be determined with several different measurements: a) lemma length; b) lemma width; c) glumae length; c) 1,000 seed weight.

Table 9 shows the 1,000 seed weights (in grams) of AM107 in comparison to other cool season turf species.

TABLE 9

1,000 Seed Weight
(Albany, Oregon - 2004/2005)

| Species | Variety | Seed Weight (gram) |
|---|---|---|
| Meadow Fescue (turf) | AMF107 | 2347 |
| Tall Fescue (turf) | Forte' | 2718 |
| Tall Fescue (turf) | Rebel II | 2368 |
| Tall Fescue (forage) | KY-31 | 3138 |
| Perennial Ryegrass (turf) | Brightstar | 1965 |
| Perennial Ryegrass (turf) | Amazing | 1754 |

Table 10 shows the lemma length (mm) of AM107 in comparison to other cool season turf species.

TABLE 10

Lemma Length
(Albany, Oregon - 2004/2005)

| Species | Variety | Lemma Length (mm) |
|---|---|---|
| Meadow Fescue (turf) | AMF107 | 5.80 |
| Tall Fescue (turf) | Forte' | 5.60 |
| Tall Fescue (turf) | Rebel II | 6.10 |
| Tall Fescue (forage) | KY-31 | 6.30 |
| Perennial Ryegrass (turf) | Brightstar | 5.80 |
| Perennial Ryegrass (turf) | Amazing | 5.53 |
| | LSD (0.05) | 0.30 |

Table 11 shows the lemma width (mm) of AM107 in comparison to other cool season turf species.

TABLE 11

Lemma Width
(Albany, Oregon - 2004/2005)

| Species | Variety | Lemma Width (mm) |
|---|---|---|
| Meadow Fescue (turf) | AMF107 | 1.33 |
| Tall Fescue (turf) | Forte' | 1.40 |
| Tall Fescue (turf) | Rebel II | 1.47 |
| Tall Fescue (forage) | KY-31 | 1.43 |
| Perennial Ryegrass (turf) | Brightstar | 1.23 |
| Perennial Ryegrass (turf) | Amazing | 1.20 |
| | LSD (0.05) | .08 |

Table 12 shows the glumae length (mm) of AM107 in comparison to other cool season turf species.

TABLE 12

Glume Length
(Albany, Oregon - 2004/2005)

| Species | Variety | Glume Length (mm) |
|---|---|---|
| Meadow Fescue (turf) | AMF107 | 4.20 |
| Tall Fescue (turf) | Forte' | 4.17 |
| Tall Fescue (turf) | Rebel II | 4.57 |
| Tall Fescue (forage) | KY-31 | 4.77 |
| Perennial Ryegrass (turf) | Brightstar | 7.37 |
| Perennial Ryegrass (turf) | Amazing | 7.17 |
| | LSD (0.05) | 0.31 |

Example 7

AM107 is the first meadow fescue to produce panics characteristics similar to turf type tall fescue. Panics characteristics are important to the number of seeds produced per plant, resulting in the overall yield of the cultivator. Cultivators which produce low seed yields are not desirable.

Meadow fescues are characterized by the inability to produce seed. Turf type tall fescue produces on average 2200 pounds per acre. The panics traits of; a) length of panics; b) spike lets per panics; c) florets per spike let; d) length of spike let contribute to the yield potential of a cultivator. Tables 13-16 illustrate that AM107 is similar to turf type tall fescue in panics characteristics.

Table 13 shows the length of the spike (cm) of AM107 in comparison to other cool season turf species.

TABLE 13

Length of Spike
(Albany, Oregon - 2004/2005)

| Species | Variety | Length of Spike (mm) |
|---|---|---|
| Meadow Fescue (turf) | AMF107 | 227.13 |
| Tall Fescue (turf) | Forte' | 204.70 |
| Tall Fescue (turf) | Rebel II | 265.79 |
| Tall Fescue (forage) | KY-31 | 286.10 |
| Perennial Ryegrass (turf) | Brightstar | 169.97 |
| Perennial Ryegrass (turf) | Amazing | 146.70 |
|  | LSD (0.05) | 19.32 |

Table 14 shows the spike lets per panics of AM107 in comparison to other cool season turf species.

TABLE 14

Spikelets per Panicle
(Albany, Oregon - 2004/2005)

| Species | Variety | Spikelets per Panicle |
|---|---|---|
| Meadow Fescue (turf) | AMF107 | 47.17 |
| Tall Fescue (turf) | Forte' | 93.40 |
| Tall Fescue (turf) | Rebel II | 101.23 |
| Tall Fescue (forage) | KY-31 | 111.87 |
| Perennial Ryegrass (turf) | Brightstar | 23.70 |
| Perennial Ryegrass (turf) | Amazing | 22.63 |
|  | LSD (0.05) | 8.72 |

Table 15 shows the number of florets per spike let of AM107 in comparison to other cool season turf species.

TABLE 15

Number of Florets per Spikelet
(Albany, Oregon - 2004/2005)

| Species | Variety | Number of Florets per Spikelet |
|---|---|---|
| Meadow Fescue (turf) | AMF107 | 6.40 |
| Tall Fescue (turf) | Forte' | 5.43 |

TABLE 15-continued

Number of Florets per Spikelet
(Albany, Oregon - 2004/2005)

| Species | Variety | Number of Florets per Spikelet |
|---|---|---|
| Tall Fescue (turf) | Rebel II | 5.27 |
| Tall Fescue (forage) | KY-31 | 5.77 |
| Perennial Ryegrass (turf) | Brightstar | 6.37 |
| Perennial Ryegrass (turf) | Amazing | 6.67 |
|  | LSD (0.05) | 0.61 |

Table 16 shows the spike let length (mm) of AM107 in comparison to other cool season turf species.

TABLE 16

Spikelet Length
(Albany, Oregon - 2004/2005)

| Species | Variety | Spikelet Length (mm) |
|---|---|---|
| Meadow Fescue (turf) | AMF107 | 14.07 |
| Tall Fescue (turf) | Forte' | 10.43 |
| Tall Fescue (turf) | Rebel II | 11.50 |
| Tall Fescue (forage) | KY-31 | 12.10 |
| Perennial Ryegrass (turf) | Brightstar | 12.17 |
| Perennial Ryegrass (turf) | Amazing | 11.06 |
|  | LSD (0.05) | 0.74 |

Example 8

AM107 is the first meadow fescue with desirable overseeing characteristics. Turf grass managers require a grass that can establish quickly and then transition rapidly. Turf grass managers also require high turf quality, a dark green color, a low vertical growth rate, and the ability to mow without shredding. Tables 14-18 shows AM107 in comparison to other grasses used in overseeded Bermuda grass.

Tables 17-21 are a summary of data collected from University overseeing trials. The trials were conducted at the University of Arkansas, Fayetteville, Ark. and Auburn University, Auburn, Ala. The trial was designed as a dual test. The entries, management, and ratings were the same at each site.

Table 17 shows the establishment rate in comparison to other grasses used in overseeded Bermuda grass turf. The data is presented on a 0-9 scale; with 9 being 100% established.

TABLE 17

Establishment Rate
(Fayetteville, Arkansas - 2004/2005)
(Auburn, Alabama - 2004/2005)

| Entry | Establishment Day 6 | | Establishment Day 12 | | Establishment Day 14 | |
|---|---|---|---|---|---|---|
|  | Arkansas | Alabama | Arkansas | Alabama | Arkansas | Alabama |
| Intermediate Ryegrass | 5.00 | 4.30 | 9.00 | 6.30 | 9.00 | 9.00 |
| Diploid Perennial Ryegrass | 3.30 | 4.80 | 7.30 | 6.80 | 9.00 | 8.80 |

TABLE 17-continued

Establishment Rate
(Fayetteville, Arkansas - 2004/2005)
(Auburn, Alabama - 2004/2005)

| Entry | Establishment Day 6 | | Establishment Day 12 | | Establishment Day 14 | |
|---|---|---|---|---|---|---|
| | Arkansas | Alabama | Arkansas | Alabama | Arkansas | Alabama |
| *Poa trivialis* | 1.00 | 1.00 | 2.30 | 2.00 | 4.30 | 6.80 |
| Meadow Fescue | 2.30 | 4.30 | 5.50 | 6.30 | 7.50 | 8.80 |
| 'T3' Tetraploid Perennial Ryegrass | 2.00 | 4.50 | 7.30 | 6.30 | 9.00 | 9.00 |
| Non-Overseeded Bermudagrass Check | 0.00 | 0.00 | 0.00 | 0.00 | 0.00 | 0.00 |
| LSD (P = .05) | 1.42 | 0.76 | 1.48 | 1.13 | 0.59 | 0.55 |

Table 18 shows the turf quality and turf color in comparison to other grasses used in overseeded Bermuda grass turf. In Table 15, the relative color and density of the different cultivators was scored using a 1-9 scale; with 9 being the darkest green or most dense.

TABLE 18

Turf Quality and Turf Color
(Fayetteville, Arkansas - 2004/2005)
(Auburn, Alabama - 2004/2005)

| Entry | Turf Quality 2004-2005 Average | | Turf Color 2004-2005 Average | |
|---|---|---|---|---|
| | Arkansas | Alabama | Arkansas | Alabama |
| Intermediate Ryegrass | 5.80 | 6.60 | 5.50 | 6.40 |
| Diploid Perennial Ryegrass | 6.70 | 6.70 | 7.40 | 6.90 |
| *Poa trivialis* | 3.40 | 6.00 | 5.10 | 5.90 |
| Meadow Fescue | 5.40 | 6.20 | 5.30 | 6.20 |
| 'T3' Tetraploid Perennial Ryegrass | 5.70 | 6.70 | 7.20 | 7.10 |
| Non-Overseeded Bermudagrass Check | 2.10 | 3.30 | 2.30 | 3.30 |
| LSD (P = .05) | 0.70 | 0.20 | 0.60 | 0.20 |

Table 19 presents the mowing quality displayed by AM107 in comparison to other grasses used in overseeded Bermuda grass turf. In Table 17, the relative mowing qualities of the different cultivators was scored using a 1-9 scale; with 9 being best.

TABLE 19

Mowing Quality
(Fayetteville, Arkansas - 2004/2005)
(Auburn, Alabama - 2004/2005)

| Entry | Mowing Quality Arkansas |
|---|---|
| Intermediate Ryegrass | 5.90 |
| Diploid Perennial Ryegrass | 6.30 |
| *Poa trivialis* | 6.10 |
| Meadow Fescue | 6.70 |
| 'T3' Tetraploid Perennial Ryegrass | 6.00 |

TABLE 19-continued

Mowing Quality
(Fayetteville, Arkansas - 2004/2005)
(Auburn, Alabama - 2004/2005)

| Entry | Mowing Quality Arkansas |
|---|---|
| Non-Overseeded Bermudagrass Check | 2.10 |
| LSD (P = .05) | 0.40 |

Table 20 helps to illustrate vertical extension. The higher the clipping yield the greater the vertical extension (growth rate) which results in frequent mowing, a non-desirable trait. The clipping yields are reported in grams per plot (Alabama data), and grams/meter$^2$ (Arkansas).

TABLE 20

Clipping Yield
(Fayetteville, Arkansas - 2004/2005)
(Auburn, Alabama - 2004/2005)

| Entry | Clipping Yield May | |
|---|---|---|
| | Arkansas | Alabama |
| Intermediate Ryegrass | 19.00 | 81.80 |
| Diploid Perennial Ryegrass | 16.20 | 65.30 |
| *Poa trivialis* | 15.70 | 67.00 |
| Meadow Fescue | 21.80 | 63.10 |
| 'T3' Tetraploid Perennial Ryegrass | 17.50 | 49.90 |
| Non-Overseeded Bermudagrass Check | 10.20 | 20.70 |
| LSD (P = .05) | 2.50 | 21.50 |

Table 21 shows the percent of Bermuda grass present of AM107 in comparison to other grasses used in overseeded Bermuda grass turf. The higher percentage relates to a more complete transition.

TABLE 21

Transition Data - % Bermudagrass
(Fayetteville, Arkansas - 2004/2005)
(Auburn, Alabama - 2004/2005)

| Entry | % Bermudagrass Present May | | % Bermudagrass Present June | | % Bermudagrass Present July | |
|---|---|---|---|---|---|---|
| | Arkansas | Alabama | Arkansas | Alabama | Arkansas | Alabama |
| Intermediate Ryegrass | 23.80 | 48.80 | 72.50 | 74.50 | 88.80 | 87.80 |
| Diploid Perennial Ryegrass | 10.00 | 48.80 | 45.00 | 74.50 | 81.30 | 84.50 |
| *Poa trivialis* | 37.50 | 40.00 | 65.00 | 53.80 | 83.30 | 67.00 |
| Meadow Fescue | 20.00 | 52.50 | 75.00 | 73.80 | 92.50 | 83.80 |
| 'T3' Tetraploid Perennial Ryegrass | 17.50 | 48.80 | 77.50 | 75.00 | 97.00 | 87.00 |
| Non-Overseeded Bermudagrass Check | 90.00 | 91.30 | 100.00 | 100.00 | 100.00 | 100.00 |
| LSD (P = .05) | 7.20 | 6.60 | 13.10 | 5.20 | 9.40 | 6.90 |

Deposit Statement

Seed of meadow fescue variety AM107 has been deposited with the American Type Culture Collection and is identified by accession number PTA 6494.

The preceding invention has been described in some detail by way of example for purposes of clarity and understanding; it will be obvious that certain changes and modifications may be practiced within the scope of the invention, as limited only by the scope of the appended claims.

We claim:

1. A meadow fescue variety AM 107, a representative sample of said variety deposited under American Type Culture Collection accession number PTA-6494.

2. A seed of the variety of claim 1.

3. A meadow fescue plant, or a part thereof, produced by growing seed of claim 2.

4. Pollen of the plant of claim 3.

5. An ovule of the plant of claim 3.

6. A meadow fescue plant, or a part thereof, having all the physiological and morphological characteristics of the meadow fescue plant of claim 3.

7. A meadow fescue produced by growing seed from the meadow fescue plant of claim 3.

8. A meadow fescue produced vegetatively from the meadow fescue plant, or a part thereof, of claim 3.

9. A method for producing turfgrass seed, comprising the steps of crossing the turfgrass plant of claim 3 with a different turfgrass plant and harvesting seed produced.

* * * * *